United States Patent [19]

Wetterlin

[11] 4,114,615
[45] Sep. 19, 1978

[54] AEROSOL INHALATION DEVICE

[75] Inventor: Kjell Ingvar Leopold Wetterlin, Sandby, Sweden

[73] Assignee: Aktiebolaget Draco, Sweden

[21] Appl. No.: 749,327

[22] Filed: Dec. 10, 1976

[30] Foreign Application Priority Data

Dec. 12, 1975 [SE] Sweden ............................ 7514066

[51] Int. Cl.² ........................................... A61M 15/00
[52] U.S. Cl. .................................. 128/173 R; 128/203
[58] Field of Search .................... 128/173 R, 203, 266, 128/205, 206, 208, 213 R; 239/309, 310

[56] References Cited

U.S. PATENT DOCUMENTS

| | | | |
|---|---|---|---|
| 1,449,047 | 4/1922 | Johnson | 128/203 |
| 1,614,532 | 1/1927 | Mobley | 222/325 |
| 2,585,254 | 2/1952 | Kochner | 239/272 |
| 2,672,144 | 3/1954 | Cohen | 128/265 |
| 2,699,167 | 1/1955 | Raiche | 128/216 |
| 2,895,651 | 7/1959 | Mahon et al. | 222/399 |
| 2,987,439 | 6/1961 | Wittlinger | 167/59 |
| 3,081,223 | 3/1963 | Gunning et al. | 167/39 |
| 3,119,561 | 1/1964 | Wilson | 239/309 |
| 3,187,748 | 6/1965 | Mitchell et al. | 128/173 R |
| 3,456,644 | 7/1969 | Thiel | 128/173 R |
| 3,605,738 | 9/1971 | Ciranna | 128/173 R |
| 3,622,053 | 11/1971 | Ryden | 128/173 R |
| 3,776,227 | 12/1973 | Pitesky | 128/203 |
| 3,809,294 | 5/1974 | Torgeson | 128/203 |
| 3,870,046 | 3/1975 | Elliott | 128/266 |
| 3,926,176 | 12/1975 | Winchell et al. | 128/1.2 |
| 3,998,226 | 12/1976 | Harris | 128/266 |

FOREIGN PATENT DOCUMENTS

| | | |
|---|---|---|
| 2,033,658 | 1/1971 | Fed. Rep. of Germany. |
| 132,993 | 11/1969 | Denmark. |
| 349,478 | 10/1972 | Sweden. |
| 107,990 | 7/1917 | United Kingdom. |
| 249,854 | 6/1927 | United Kingdom. |
| 922,310 | 3/1963 | United Kingdom. |
| 329,778 | 5/1930 | United Kingdom. |
| 830,427 | 3/1960 | United Kingdom. |
| 977,894 | 12/1964 | United Kingdom. |
| 1,269,811 | 4/1972 | United Kingdom. |

OTHER PUBLICATIONS

Derwent Patent Abstract No. 88758V.
Swedish Disclosure No. 7014820-0.
Derwent Patent Abstract No. 27633R.
Derwent Patent Abstract No. 63133T.
Derwent Patent Abstract No. 64980V.

Primary Examiner—Robert W. Michell
Assistant Examiner—Henry J. Recla
Attorney, Agent, or Firm—Brumbaugh, Graves, Donohue & Raymond

[57] ABSTRACT

An aerosol inhalation device for dispensing medicine makes use of separate propellant and medicine containers. A valve is provided, which acts in conjunction with a metering chamber, to supply a measured amount of propellant upon each activation of the device.

7 Claims, 4 Drawing Figures

AEROSOL INHALATION DEVICE

BACKGROUND OF THE INVENTION

The present invention relates to aerosol inhalation devices for application of medication to the respiratory tract.

Aerosol inhalation devices are primarily used for local application of medications to the lower parts of the respiratory tract. Such local administration of medication results in rapid response to the medication with a low dosage as compared to systematic administration of the same drug.

Aerosol devices for administration of medication must be designed to have suitable spraying properties, which are reproducible during the useful lifetime of the inhalation device. In order to achieve uniform spraying properties, it is neccessary for the propellant pressure of the device to remain constant. The propellant pressure should be also selected to be adequate to produce a fine spray. If spray particles are excessively large, they will be deposited primarily in the oral cavity or upper respiratory tract.

Conventional inhalation devices, such as described in U.S. Pat. Nos. 3,001,524 and 3,012,555 make use of a comparatively large container having both medication and propellant, which is permanently mounted to a dispensing unit. The medication is either dissolved or suspended in the propellant which is typically a chlorofluoroalkane, such as Freon. ® Such fluorocarbon-type propellants have a pressure of 0.3 to 0.5 $\times 10^6$ Pascal (3000 to 5000 gm/cm$^2$) at room temperature and have previously been considered to have low toxicity. Fluorocarbon propellants have therefore gained wide use in inhalation devices as well as many other aerosols. Recently, the toxicity of fluorocarbon propellants has been questioned, and recommendations have been made to use substitute propellants in medical inhalation devices (see Toxicology 3 (1975), pp. 321–332). In addition, some scientists have raised questions regarding the possibility that fluorocarbon propellants contribute to the depletion of the atmospheric ozone layer.

Prior inhalation devices have further disadvantages since the permanent mounting of the dispensing apparatus to the medication container results in the disposal of the rather expensive dispensing apparatus when the container is empty. Further, the available pressure in these units is limited by the container to no more than 0.5 $\times 10^6$ Pascals. (5000 gm/cm$^2$) This is a distinct disadvantage, since higher propellant pressure can produce in a more finely divided aerosol spray, resulting in more rapid propellant evaporation and more uniform medication distribution within the respiratory tract. Another problem with prior aerosol devices is that they are susceptible to excess use by the patient. These devices permit medication to be applied with each breath and contain sufficient medication for approximately 200–400 inhalations. The patient may therefore tend to apply more medication than is appropriate.

While it is evident that it is desirable in an inhalation device to use a non-toxic propellant, such as carbon dioxide, prior art aerosol mechanisms using carbon dioxide as a propellant are not appropriate for use in inhalation devices. Prior art carbon dioxide propelled mechanisms make use of dissolved carbon dioxide to produce spraying pressure. This is unsuitable for an aerosol inhalation device because the propellant pressure decreases as the contents of the container are reduced. Such decrease in propellant pressure reduces the ability of the inhalation device to apply medication to the lower respiratory tract.

It is therefore an object of the present invention to provide an aerosol inhalation device capable of using propellants other than fluorocarbons.

It is a further object of the invention to provide such a device with uniform aerosol properties.

It is a still further object of the invention to provide such a device which does not lend itself to excess use by the patient.

SUMMARY OF THE INVENTION

In accordance with the present invention, there is provided an aerosol inhalation device for dispensing a unit dosage of medication upon each activation. The device includes a propellant container, a propellant metering chamber, a container for holding a unit dosage of the medication and an inhalation outlet. A propellant passage is provided interconnecting the metering chamber, the container and the outlet. A valve alternately connects the metering chamber with the propellant container and the propellant passage.

In a preferred embodiment, the device includes a reservoir chamber adjacent the metering chamber and connected to the propellant container. The valve means includes a displaceable valve member having a passage which connects the metering chamber and the reservoir chamber in a first position and connects the metering chamber with the propellant passage in a second position. The valve member may be equipped with a spring for returning it to the first position after activation. The propellant container may be equipped with a penetrable membrane which is opened upon activation of a perforating member on the inhalation device. The propellant container may be enclosed in a protective case and sealed against the remaining portions of the inhalation device to prevent leakage. A locking plate may be provided to prevent removal of the protective cover without release of pressure. The inhalation outlet may include a piston, activated by patient breathing and connected to activate a discharge of a measured amount of propellant. Where the medication is in liquid form, the inhalation outlet may be provided with a medication container having a capillary passage opening adjacent the opening of the propellant passage. Where the medication is in powder form, the propellant passage may be directed into a medication container and thence to the inhalation outlet. Portions of the aerosol inhalation device may also be used as a propellant and dispensing unit for other aerosol applications.

For a better understanding of the present invention, together with other and further embodiments, reference is made to the following description taken in conjunction with the accompanying drawings, and its scope will be pointed out in the appended claims.

DESCRIPTION OF THE INVENTION

Figure 1:
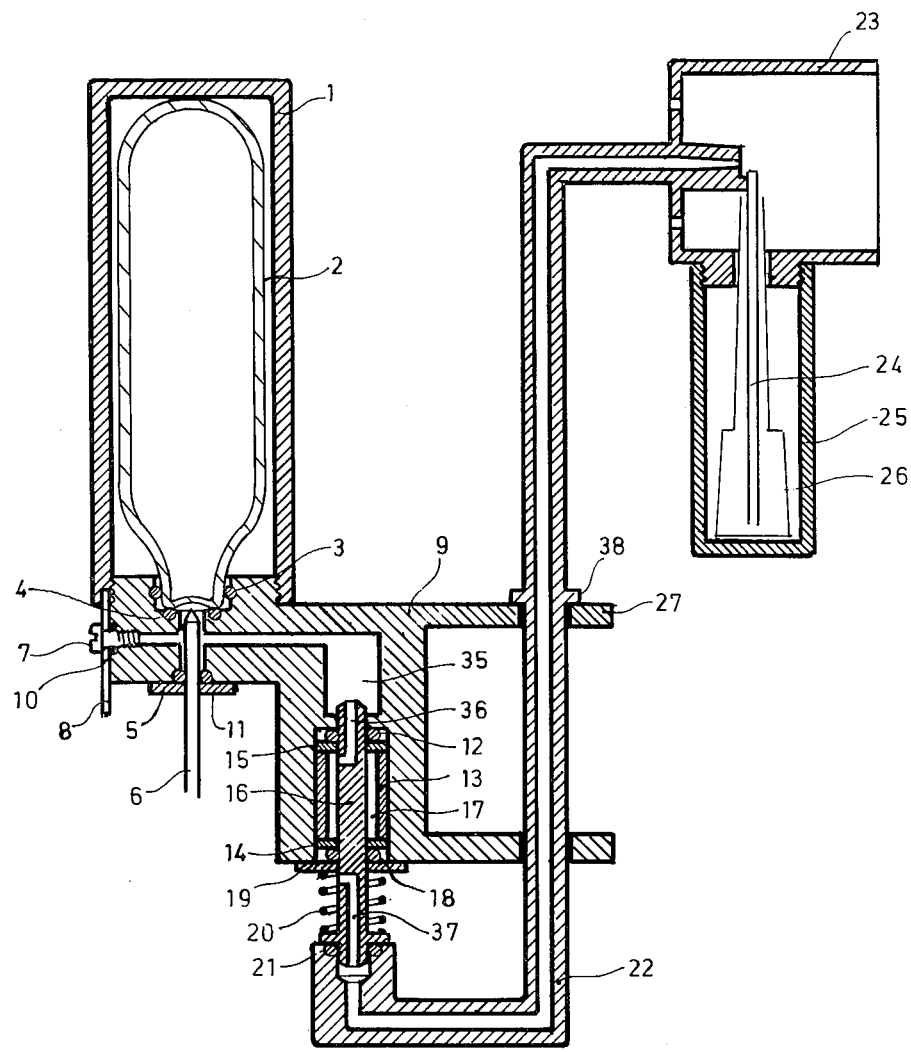
FIG. 1 is a cross-sectional view of a liquid medication inhalation device in accordance with the present invention.

The inhalation device illustrated in FIG. 1 includes a propellant container 2 which is initially filled with a liquid propellant, such as liquid carbon dioxide. Propellant container 2 is arranged within a protective cover 1 which is threaded onto the main body 9 of the inhalation device. The bottom portion of container 2 is equipped with a membrane, which may be perforated by activation of a moveable perforating pin 6. Container 2 and pin 6 are sealed to the body 9 of the inhalation device by O-rings 3, 4, and 5. O-ring 5 is maintained in position against pin 6 by retaining ring 11. The perforated opening at the bottom of the propellant container 2 communicates with a reservoir chamber 35. Immediately below reservoir chamber 35, there is provided a propellant metering chamber 17, which has a volume, regulated by sleeve 13, which corresponds to the appropriate amount of liquid propellant required for activation of the aerosol device to supply a single dose of medication to the patient.

A propellant passage 22 interconnects metering chamber 17 with inhalation outlet 23, which is arranged for insertion in the patient's mouth and may be vented to permit breathing. A valve member 16 connected to passage 22 is centrally arranged in chamber 17 and is movable in a vertical direction in FIG. 1. Passage 36 in the upper part of valve member 16 connects chamber 17 with reservoir chamber 35 when valve member 16 is in its lowermost position. When valve member 16 is moved in an upward direction, passage 36 is closed. Further upward movement of the valve member 16 causes a second passage 37 to open into chamber 17 thereby connecting chamber 17 with propellant passage 22 and permitting the liquified propellant in the propellant metering chamber to expand during movement through passage 22 to inhalation outlet 23. Following this activation of valve member 16, the member may be allowed to move in a downward direction under the influence of spring 20 until passage 37 is closed. In its lowermost position, passage 36 will again connect chamber 17 to reservoir chamber 35. O-rings 12, 18, and 21 are provided for sealing valve member 16 and are retained in position by retaining rings 14, 15, and 19. A stop 38 is arranged on propellant passage 22 to engage a portion 27 of body 9 and hold valve 16 in its lowermost position against the propellant pressure acting on valve member 16.

When the medication to be applied is in a liquid form, it may be conveniently supplied in a single dose container 26 which is equipped with capillary tube 24. Container 26 is positioned within protective chamber 25 and arranged so that the upper opening of capillary tube 24 is immediately adjacent the opening of propellant passage 22 in inhalation outlet 23. Activation of the device by upward movement of propellant passage 22 provides a measured amount of propellant from chamber 17 which in passage across the top of capillary 24 draws the unit dosage of medicine from container 26. The position of capillary 24 may be adjusted to achieve optimum spray conditions. Upon release, passage 22 returns to the position shown in FIG. 1 permitting a new measured amount of propellant to enter into metering chamber 17 from reservoir 35.

The protective cover 1 is locked into position over propellant chamber 2 by locking plate 8. Plate 8 is maintained in position by screw 7 which is threaded into a passage opening into reservoir chamber 35 and sealed with O-ring 10. Protective cover 1 cannot be removed from the inhalation device without unscrewing screw 7 and therefore venting reservoir chamber 35 and propellant container 2. This prevents removal of the protective cover while a dangerous amount of pressure exists within the device. This is necessary because of the relatively high pressure of liquid carbon dioxide, $5 \times 10^6$ Pascal (50000 gm/cm$^2$) at room temperature.

While it is possible to make use of conventional propellant fluids such as fluorocarbons, propellant chamber 2 is preferably filled with liquid carbon dioxide. Carbon dioxide, when vaporized, presents no hazard to the environment and is safely used without damage to the internal portions of the respiratory tract.

Figure 2:
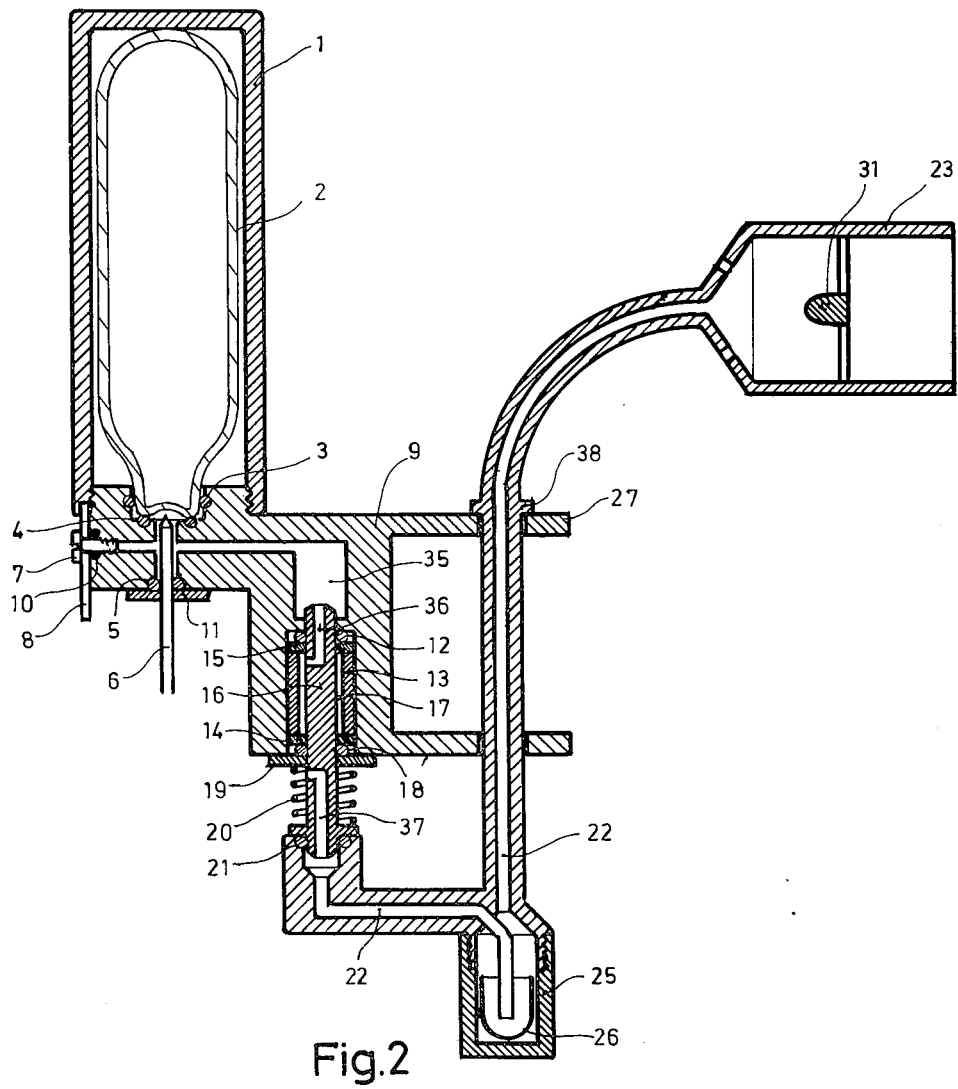
FIG. 2 is a cross-sectional view of a powdered medication inhalation device in accordance with the present invention.

FIG. 2 shows an alternate embodiment of the invention wherein the medication container 26 is designed for use with powdered medication. The container 26 is arranged within a protective cover 25. Propellant passage 22 enters the container in a manner such that the propellant vapors drive the powder up the remaining portion of propellant passage 22 into inhalation outlet opening 23. Outlet 23 is provided with a protective member 31 in the form of hemispherical body which is arranged to prevent large agregate particles of medication from being driven into the respiratory passage. Container 26 may be an open capsule as illustrated or may be a closed capsule which is perforated upon insertion into the device.

Figure 3:
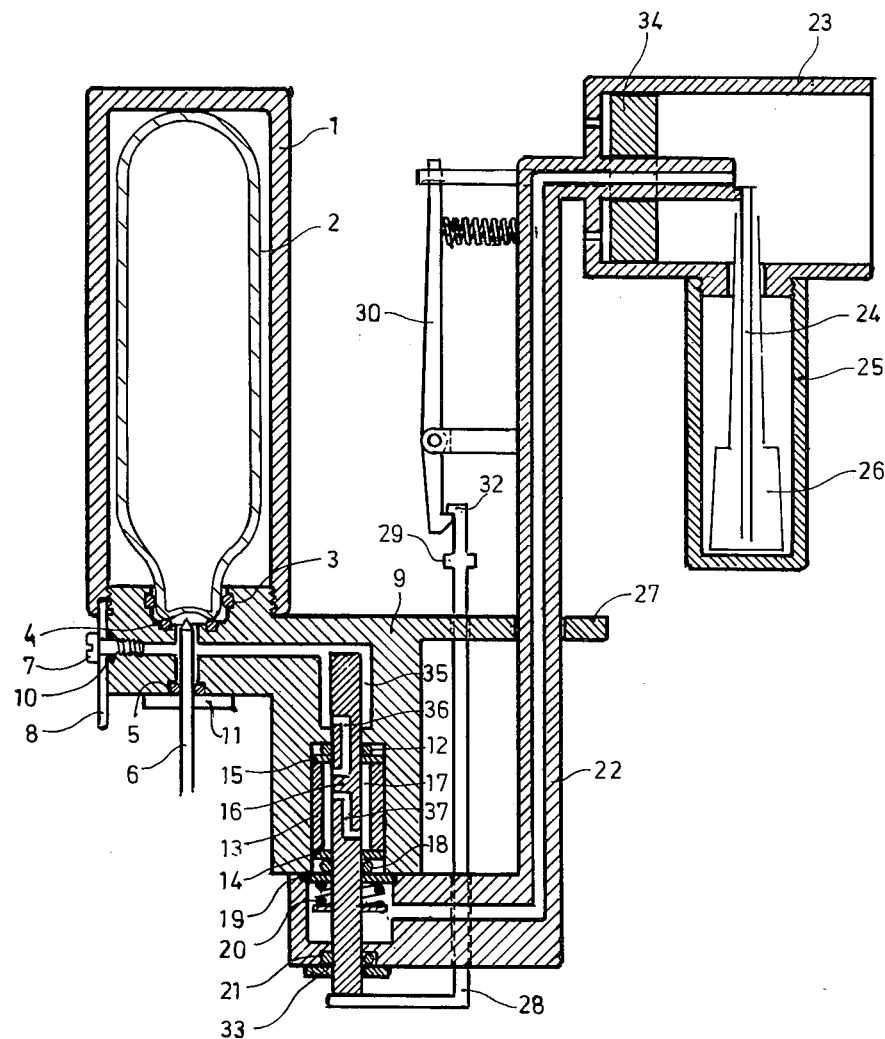
FIG. 3 is a cross-sectional view of a breathing activated liquid medication inhalation device in accordance with the present invention.
Figure 4:
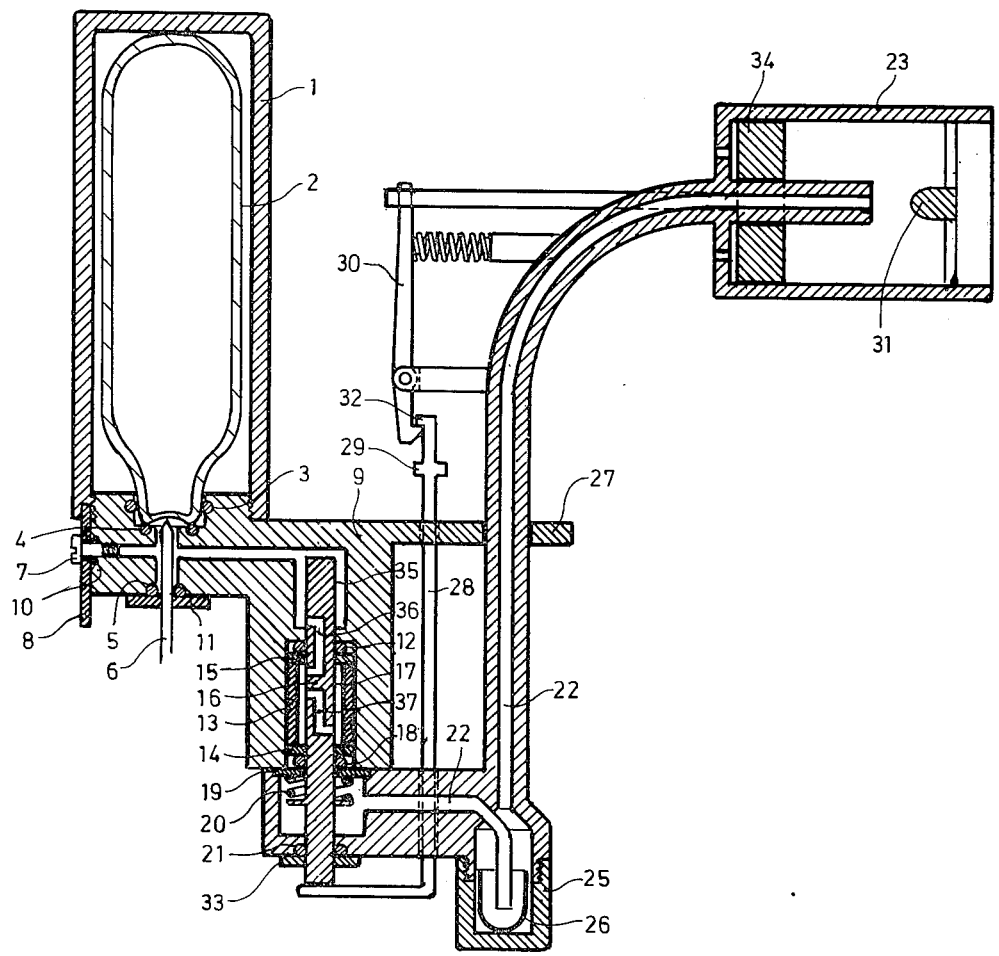
FIG. 4 is a cross-sectional view of a breathing activated powdered medication inhalation device in accordance with the present invention.

The inhalation devices of FIGS. 3 and 4 are similar to those of FIGS. 1 and 2, but they are equipped for automatic activation of the dispensing valve in response to inhalation by the patient thus attaining aerosol activation at the correct phase of breathing. In the FIGS. 3 and 4 embodiments, valve member 16 is arranged to connect reservoir chamber 35 with metering chamber 17 when valve member 16 is in the uppermost position and to connect propellant passage 22 with metering chamber 17 when valve member 16 is in the lowermost position. A connecting arm 28 is arranged between valve member 16 and activating arm 30, which is equipped with a spring and connected to piston 34. The end of arm 28 is provided with lug 32 for engaging activating arm 30 and stop 29 for limiting its downward motion. When the device is in the cocked position shown and piston 34 is drawn to the right as a result of inhalation by a patient through outlet 23, arm 30 pivots away from lug 32, permitting the downward motion of connecting arm 28 under the influence of gas pressure and spring 20. The downward motion of valve member 16 release the propellant in metering chamber 17 into propellant passage 22. Connecting arm 28 along with valve member 16, must be manually moved to the cocked position shown in FIG. 3 prior to further operation of the device.

It will be recognized that prior to each activation of the device, the container holding the medicine, liquid or powder, must be replaced. This may be done manually in accordance with the embodiments illustrated in the drawings, or may be achieved automatically by having a set of unit dose containers arranged on a revolving magazine or a continuous belt. Subsequent doses may be moved into position following each activation of the device either manually or through a lever connected to valve member 16.

While the present invention is primarily directed to medicinal inhalation devices, it will be recognized that the propellant portions of the device are generally useful for aerosol products. The propellant passage 22 may therefore be equipped with a coupling to a conventional aerosol can so that the can is supplied with additional propellant on each activation of the device. The coupling may be arranged to open the can valve upon connection.

While there has been described what are believed to be the preferred embodiments of the invention, those skilled in the art will recognize that other and further modifications may be made thereto without departing from the spirit of the invention, and it is intended to claim all such embodiments as fall within the true scope of the invention.

I claim:

1. An aerosol inhalation device for dispensing unit dosages of medication, comprising:
   a housing;
   a propellant container mounted to said housing;
   a protective case mounted to said housing and enclosing said propellant container;
   a first passage in said housing having one end connected to said propellant container;
   an opening in said housing connecting said first passageway to the outer surrounding;
   a locking plate retaining said protective cover in position on said housing;
   a screw holding said locking plate and sealing said opening between said first passage and the outer surrounding;
   an inhalation outlet;
   a second passage having one end opening in said inhalation outlet;
   a valve connected between the outer ends of said first and second passages and including a metering chamber means for alternately connecting said metering chamber with said first and second passages on operation of said valve;
   and a medication container for holding a unit dose of said medication having an outlet an communication with said one end of said second passage to cause propellant flowing through said second passage to propel said medication into said inhalation outlet.

2. An inhalation device as specified in claim 1 wherein there is additionally provided a reservoir chamber adjacent said metering chamber and connected to said first passage and wherein said valve means comprises a valve member displaceably mounted in said metering chamber, between first and second positions, said valve member having a first valve passage for interconnecting said reservoir chamber and said metering chamber in said first position and a second valve passage interconnecting said metering chamber and said second passage in said second position.

3. An inhalation device as specified in claim 2 wherein there is provided a spring for returning said valve member from said second to said first position.

4. An inhalation device as specified in claim 1 wherein said propellant container is sealed by a membrane, and wherein said inhalation device is provided with moveable means for perforating said membrane.

5. An inhalation device ase specified in claim 1 wherein said medication is a liquid, and wherein said medication container includes a capillary passage with an opening adjacent said passage opening in said inhalation outlet.

6. An inhalation device as specified in claim 1 wherein said medication is a powder, wherein said medication container comprises a chamber and wherein said second passage includes a first passage portion connecting said valve and said chamber and a second passage portion connecting said chamber and said passage opening, whereby propellant flowing through said second passage flows through said chamber and propels said powder through said second passage portion to said inhalation outlet.

7. An inhalation device as specified in claim 1 wherein there is provided a piston in said inhalation outlet, moveable by air flow in said outlet, and wherein there is provided linkage connecting said valve and said piston to cause activation of said valve in response to movement of said piston.

* * * * *

UNITED STATES PATENT OFFICE
CERTIFICATE OF CORRECTION

Patent No. 4,114,615    Dated September 19, 1978

Inventor(s) Kjell Ingvar Leopold Wetterlin

It is certified that error appears in the above-identified patent and that said Letters Patent are hereby corrected as shown below:

Col. 5, line 36, "outer" should read --other--;
Col. 5, line 38, after "chamber" insert a comma;
Col. 5, line 42, after "medication" insert --and--; and
Col. 6, line 22, "ase" should read --as--.

*Signed and Sealed this*

*Twentieth* Day of *March 1979*

[SEAL]

Attest:

RUTH C. MASON
*Attesting Officer*

DONALD W. BANNER
*Commissioner of Patents and Trademarks*